(12) United States Patent
Renard et al.

(10) Patent No.: US 11,207,075 B2
(45) Date of Patent: Dec. 28, 2021

(54) ELEMENT FOR PRODUCING A VASCULAR CLIP AND VASCULAR CLIP PRODUCED IN THAT WAY

(71) Applicant: Xavier Renard, Vauhallan (FR)

(72) Inventors: Xavier Renard, Vauhallan (FR); Jean-Baptiste Renard, Brussels (BE)

(73) Assignee: Xavier Renard, Vauhallan (FR)

( * ) Notice: Subject to any disclaimer, the term of this patent is extended or adjusted under 35 U.S.C. 154(b) by 130 days.

(21) Appl. No.: 16/630,619

(22) PCT Filed: Jul. 3, 2018

(86) PCT No.: PCT/FR2018/000185
§ 371 (c)(1),
(2) Date: Jan. 13, 2020

(87) PCT Pub. No.: WO2019/012190
PCT Pub. Date: Jan. 17, 2019

(65) Prior Publication Data
US 2020/0155157 A1      May 21, 2020

(30) Foreign Application Priority Data
Jul. 12, 2017   (FR) ..................................... 17 70747

(51) Int. Cl.
*A61B 17/122*      (2006.01)
*A61B 17/00*       (2006.01)

(52) U.S. Cl.
CPC .. *A61B 17/122* (2013.01); *A61B 2017/00862* (2013.01)

(58) Field of Classification Search
CPC ... A61B 17/122; A61B 17/1227; A61F 6/206; Y10T 24/15; Y10T 24/44291;
(Continued)

(56) References Cited

U.S. PATENT DOCUMENTS

| | | | | |
|---|---|---|---|---|
| 2,782,482 A | * | 2/1957 | Baril ....................... | D06F 55/00 24/501 |
| 3,096,551 A | * | 7/1963 | Shoberg ................. | H02G 11/00 24/132 R |

(Continued)

FOREIGN PATENT DOCUMENTS

EP             0105414       4/1984
WO    WO 2004/073487       9/2004

OTHER PUBLICATIONS

International Search Report, PCT/FR2018/000185, dated Oct. 30, 2018.

*Primary Examiner* — Ryan J. Severson
(74) *Attorney, Agent, or Firm* — Nixon & Vanderhye

(57) ABSTRACT

Disclosed are elements for producing a vascular clip and vascular clips produced with these elements. The element is essentially characterized by the fact that it includes a support plate, a clip tab including a gripping face, a unit for securing the clip tab and the edge face of the plate, two substantially identical brackets, each bracket substantially having the shape of a cylinder sector with a thickness Ep and including a through hole with an axis parallel to the generatrix of the cylinder, and a unit to secure the two brackets and the plate in such a way that the axes of the two holes are located on the same straight line perpendicular to the tab and that the opposite faces of the two brackets are set apart from each other by a value equal to the thickness Ep.

20 Claims, 1 Drawing Sheet

(58) Field of Classification Search
CPC ......... Y10T 24/44376; Y10T 24/44385; Y10T 24/44393; Y10T 24/44462; Y10T 24/4447; Y10T 24/44479
See application file for complete search history.

(56) References Cited

U.S. PATENT DOCUMENTS

| | | | | |
|---|---|---|---|---|
| 3,326,217 A * | 6/1967 | Kerr | ................... | A61B 17/1227 606/158 |
| 3,598,125 A | 8/1971 | Cogley | | |
| 4,175,306 A * | 11/1979 | Bigelow | ............... | A47G 25/485 24/507 |
| 4,487,205 A * | 12/1984 | Di Giovanni | ........ | A61B 17/122 606/158 |
| 4,800,879 A | 1/1989 | Golyakhovsky et al. | | |
| 4,932,955 A * | 6/1990 | Merz | ................... | A61B 17/1227 24/510 |
| 4,957,500 A * | 9/1990 | Liang | ..................... | A61B 17/02 606/157 |
| 5,059,202 A * | 10/1991 | Liang | ..................... | A61B 17/11 606/150 |
| 5,079,808 A * | 1/1992 | Brown | ...................... | B42F 1/02 24/499 |
| 5,103,839 A | 4/1992 | Shichman | | |
| 5,571,125 A | 11/1996 | Chadwick | | |
| 5,846,255 A * | 12/1998 | Casey | ................... | A61B 17/122 606/157 |
| 6,302,366 B1 * | 10/2001 | Saylor | .................... | B42F 1/006 24/489 |
| 6,699,258 B1 * | 3/2004 | Sadler | ................. | A61B 17/122 606/157 |
| 7,144,402 B2 * | 12/2006 | Kuester, III | ....... | A61B 17/1227 606/158 |
| 7,780,688 B2 * | 8/2010 | Sakakine | ........... | A61B 17/1227 606/157 |
| 8,273,096 B2 * | 9/2012 | Lazic | ................. | A61B 17/1227 606/158 |
| 8,348,251 B2 * | 1/2013 | Gallo | .................... | D05B 35/02 269/3 |
| 9,358,008 B2 * | 6/2016 | Mazzucco | ........... | A61B 17/122 |
| 9,386,987 B2 * | 7/2016 | Lazic | ................. | A61B 17/1227 |
| 10,226,252 B2 * | 3/2019 | Lazic | ................. | A61B 17/1227 |
| 10,278,700 B2 * | 5/2019 | Mazzucco | ........... | A61B 17/083 |
| 2004/0254596 A1 * | 12/2004 | Kuester, III | .......... | A61B 90/92 606/158 |
| 2006/0100646 A1 * | 5/2006 | Hart | ................... | A61B 17/1227 606/151 |
| 2007/0112365 A1 * | 5/2007 | Hilal | ................... | A61B 17/122 606/157 |
| 2013/0289586 A1 | 10/2013 | Mazzucco et al. | | |
| 2015/0289876 A1 * | 10/2015 | Lazic | ..................... | A61B 17/11 606/153 |
| 2016/0051260 A1 * | 2/2016 | Renard | ................. | A61B 17/11 606/158 |
| 2016/0089144 A1 * | 3/2016 | Mazzucco | ........... | A61B 17/083 606/221 |
| 2020/0155157 A1 * | 5/2020 | Renard | .............. | A61B 17/1227 |

* cited by examiner

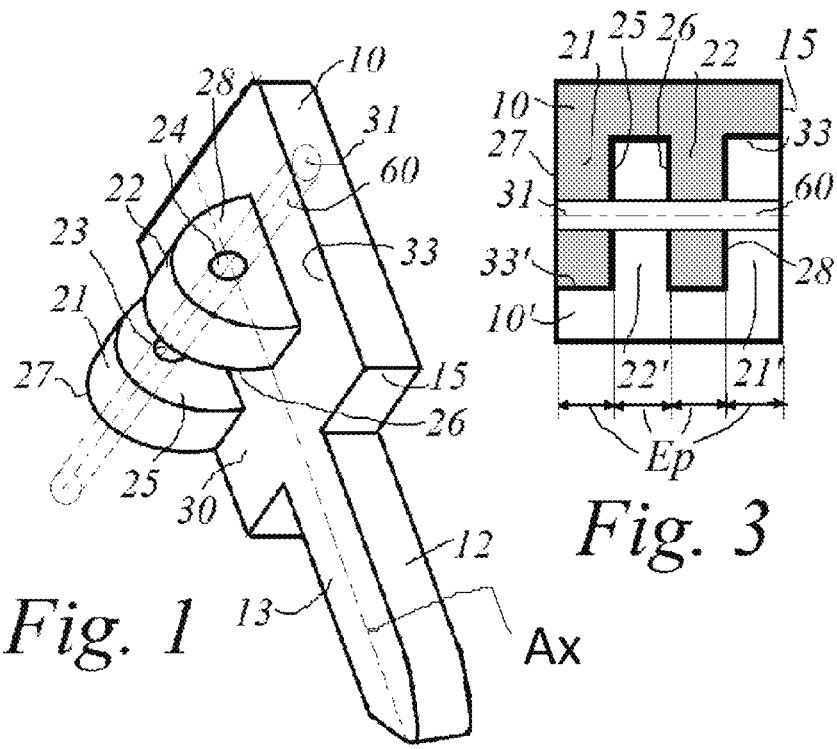
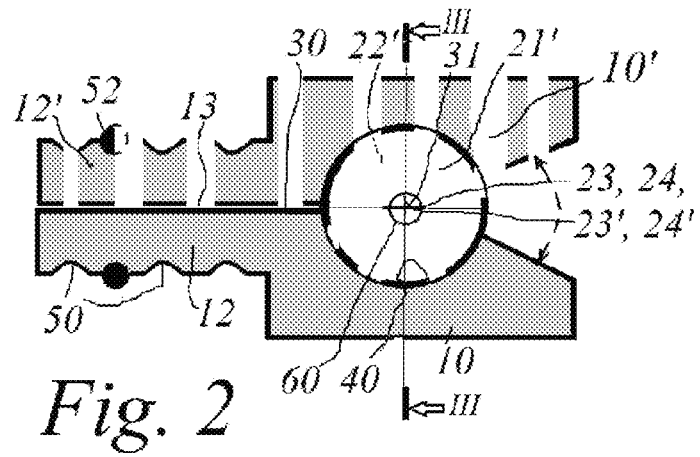

ELEMENT FOR PRODUCING A VASCULAR CLIP AND VASCULAR CLIP PRODUCED IN THAT WAY

BACKGROUND OF THE INVENTION

Field of the Invention

This invention relates to an improvement on the elements for producing a vascular clip and vascular clips produced with these elements.

Description of Art the Related

Elements for producing vascular clips are already known. For example, such elements have been described and illustrated in U.S. Pat. No. 5,571,125, EP 0105414, U.S. Pat. No. 5,103,839 and WO 2004/073487.

These elements for producing a vascular clip are relatively satisfactory, but still have drawbacks, mainly because of their very small dimensions.

SUMMARY OF THE INVENTION

Thus, this invention proposes an element for producing a vascular clip that essentially overcomes the drawbacks of similar elements of the prior art, and also a vascular clip produced with these elements, the structure of which particularly allows production for a lower manufacturing cost price, while imparting to this clip clamping characteristics that are better than those of vascular clips of the prior art, even though its size is minimal, which is very important for the applications of these clips, for example to join or hold very small blood vessels such as those that can be found in human hands.

More precisely, this invention is aimed at an element to make a vascular clip that comprises:
- a support plate,
- a clip tab with a gripping face, which defines a longitudinal axis,
- means for securing said clip tab with the edge face of said plate,
- two substantially identical brackets, each substantially having the shape of a cylinder sector with thickness Ep taken along a line parallel to the generatrix defining the cylinder sector, with a through hole having a definite diameter and an axis parallel to said generatrix,
- means for securing the two brackets and a face portion of said plate in such a way that the axes of the two through holes are located along the same straight line perpendicular to the longitudinal axis of said clip tab and the opposite faces of the two brackets are set apart from each other by a value equal to the thickness Ep,

BRIEF DESCRIPTION OF THE DRAWINGS

Other characteristics and benefits of this invention will become clearer in the description below, provided by reference to the drawings attached for the purposes of illustration, which are not imitative in any way, in which:

FIG. 1 is a cavalier perspective view of a first embodiment of an element according to the invention for producing a vascular clip, FIG. 2 is a side view of a vascular clip according to the invention made with two elements according to the invention produced in a second embodiment, and FIG. 3 is a cross-sectional view of the vascular clip along the plane III-III defined in FIG. 2.

DESCRIPTION OF THE PREFERRED EMBODIMENTS

It must be noted that in this description, when the adverb "substantially" is associated with a qualifier of a given means, that qualifier is to be understood in the strict or approximate meaning.

Particularly by reference to FIG. 1, this invention relates to an element for producing a vascular clip, that element comprising a support plate 10 preferably in the shape of a right-angled parallelepiped, as illustrated in FIG. 1.

The element further comprises a clip tab 12 comprising a gripping face 13 and defining a longitudinal axis, means for securing the clip tab and the edge face 15 of the plate 10, two substantially identical brackets 21, 22, each bracket having substantially the shape of a cylinder sector, for example, advantageously the shape of a half cylinder of revolution.

Each bracket 21, 22 has a thickness with a value Ep, which dimension is taken along a line parallel to the generatrix defining the cylinder sector, and a through hole 23, 24 with a definite diameter, the axis of that through hole being parallel to the generatrix defining the cylinder.

The element further comprises means for securing the two brackets 21, 22 and a face portion 30 of the plate 10 in such a way that the axes of the two through holes 23, 24 are located along the same straight line 31 perpendicular to the longitudinal axis of the clip tab 12 and the opposite faces 25, 26 of the two brackets 21, 22 are set apart from each other by a value equal to the thickness Ep.

The means for securing the clip tab 12 and the edge face 15 of the plate 10 and the means for securing the two brackets 21, 22 and a face portion 30 of the plate 10 may be of any type. However, in a very preferable and economically advantageous embodiment, they are achieved by the fact that the clip tab 12, the two brackets 21, 22 and the plate 10 are made up of a single piece by molding plastic or similar material, so that those four parts are effectively secured to each other.

In a very preferable embodiment, the means for securing the two brackets 21, 22 and the face portion 30 of the plate 10 are arranged in such a way that one 21 of the two brackets has a face 27 located on the plane of an edge of the edge face 15 of the plate 10 perpendicular to the straight line 31, and that the face portion 30 is substantially flat, the width of that face portion 30 taken along a direction parallel to that straight line 31 being at least equal, if not equal to four times the thickness Ep so as to define, on this face portion 30, a free part 33 with width at least equal to Ep, which free part 33 borders the face 28 of the other bracket 22 that is the farthest away from the face 27 of the bracket 21 located on the plane of an edge of said edge face 15, by reference to FIGS. 1 and 3.

Always in a very preferable embodiment, the means for securing the clip tab 12 and the edge face 15 of the plate 10 are arranged in such a way that the face portion 30 and the gripping face 13 of the clip tab 12 are substantially coplanar, by reference to FIGS. 1 and 2.

Always in another very preferable embodiment, the means for securing the two brackets 21, 22 and the face portion 30 of the plate 10 are arranged in such a way that the collinear axes of the two holes 23, 24 of the two brackets 21, 22 are substantially located on that face portion 30, by reference to FIGS. 2 and 3.

Advantageously, the element according to the invention for producing a vascular clip further comprises two recesses, the first of which is located between the two brackets 21, 22 and the second 40 is made in the free part 33 of the plate portion 30, the second recess bordering the face 28 of the bracket 22 that is opposite the free part 33 of the plate portion 30, and these first and second recesses being made in such a way as to allow the rotation of the two brackets 21, 22 of a first element mounted in engagement with a second element identical to the first one in such a way that the axes of the four holes 23, 24, 23', 24' of the four brackets are collinear, with the two brackets 21' 22' of the second element, by reference to FIGS. 2 and 3.

In another very preferable embodiment, the element according to the invention comprises notches 50, FIG. 2, made on at least one exterior face of the clip tab 12, that is to say other than the gripping face 13, to create positioning marks for an elastic ring 52, the function of which will be explained below.

This invention also relates to a vascular clip that is made up of the assembly of two identical elements such as those described above, the two elements being assembled, in FIGS. 2 and 3, in such a way that one (in continuous lines in FIG. 2) of the two brackets 21, 22 of one of the two elements is fitted between the two brackets 21', 22' of the other element (in dashed lines in the same FIG. 2) and that the four holes 23, 24, 23', 24' are collinear, and of a rotation pin 60 with a diameter equal to the diameter of the four holes, which rotation pin is fitted in the four holes.

Further, that embodiment makes it possible to provide at least one elastic ring 52 suitable for being placed in one of the notches 50 so as to externally surround the two clip tabs 12, 12' of the two assembled elements to apply a clamping force, for example on a blood vessel, with an intensity that is particularly determined by the practitioners.

In that last case, the elastic ring 52 has a shape designed to apply radial tensile force in given value T that is substantially based on the formula:

$$T = \frac{-2E(R - Ro)}{Ro}$$

wherein E is the Young's modulus of the elastic material and Ro and R are the average radii of the ring when unstrained and strained, respectively.

The description above of the element and the vascular clip is sufficient along with the knowledge of the prior art to understand the working of the vascular clip, which will not be described further in this document.

However, it must be noted that the vascular clip produced with two elements according to the invention offers definite benefits, as mentioned in the introduction to this description. In particular, it is made with two identical elements, which reduces its manufacturing cost, particularly by molding, as only one mold is needed. Further, since this vascular clip is perfectly symmetrical, when the tabs 12 and 12' are applied against a blood vessel, for instance in a hand during an operation, it does not tend to twist and the clamping force remains fully applied to the blood vessel, particularly because the clamping surfaces of each of the two elements are substantially parallel.

The invention claimed is:

1. An element for producing a vascular clip, comprising:
   a support plate (10);
   a clip tab (12) with a gripping face (13) and defining a longitudinal axis;
   means for securing said clip tab and an edge face (15) of said plate (10);
   two substantially identical brackets (21, 22), each substantially shaped as a cylinder sector with a thickness Ep taken along a line parallel to the generatrix defining the cylinder sector, with a through hole (23, 24) having a definite diameter and an axis parallel to said generatrix; and
   means for securing the two brackets and a face portion (30) of said plate (10) in such a way that the axes of the two through holes (23, 24) are located along a same straight line (31) perpendicular to the longitudinal axis of said clip tab (12), and opposite faces (25, 26) of the two brackets (21, 22) are set apart from each other by a value equal to the thickness Ep,
   wherein said means for securing the two brackets (21, 22) and the face portion (30) of said plate (10) are arranged in such a way that a first (21) of the two brackets has a face (27) located on a plane of an edge of the edge face (15) of the plate (10) perpendicular to said straight line (31),
   and said face portion (30) is substantially flat, a width of the face portion along a direction parallel to said straight line (31) being at least substantially equal to four times the thickness Ep so as to define, on the face portion (30), a free part (33) bordering a face (28) of a second (22) of the two brackets that is farthest away from the face (27) of the first bracket (21) located on the plane of the edge of said edge face (15).

2. The element according to claim 1, wherein said means for securing the clip tab (12) and the edge face (15) of the plate (10) are arranged in such a way that the face portion (30) and the gripping face (13) of the clip tab (12) are substantially coplanar.

3. The element according to claim 2, wherein said means for securing the two brackets (21, 22) and the face portion (30) of said plate (10) are arranged in such a way that the axes of the two through holes (23, 24) of the two brackets (21, 22) are substantially located on said face portion (30).

4. The element according to claim 3, further comprising: two recesses, a first of said two recesses located between the two brackets (21, 22) and a second (40) of said two recesses is made in the free part (33) of the plate portion (30), the second recess bordering the face (28) of the second bracket (22) that is opposite the free part (33) of the plate portion (30), and the first and second recesses are made in such a way as to allow rotation of the two brackets (21, 22) of a first element mounted in engagement with a second element identical to the first element in such a way that axes of the holes (23, 24, 23', 24') of the four brackets are collinear, with two brackets (21' 22') of the second element.

5. The element according to claim 4, further comprising: notches (50) made on said clip tab (12) forming position references for an elastic ring (52).

6. A vascular clip comprised of:
   an assembly of two identical said elements of claim 5, the two elements being assembled in such a way that one of the two brackets (21, 22) of a first of the two elements is fitted between two brackets (21', 22') of a second of the two elements and that axes of holes (23, 24, 23', 24') of the four brackets are collinear; and
   a rotation pin (60) with a diameter equal to a diameter of the holes, said rotation pin fitted in the holes.

7. The vascular clip according to claim 6, further comprising:
at least one elastic ring (52) that externally surrounds the clip tabs of the two assembled elements, said elastic ring being located in one of the notches (50).

8. A vascular clip comprised of:
an assembly of two identical said elements of claim 4, the two elements being assembled in such a way that one of the two brackets (21, 22) of a first of the two elements is fitted between two brackets (21', 22') of a second of the two elements and that axes of holes (23, 24, 23', 24') of the four brackets are collinear; and
a rotation pin (60) with a diameter equal to a diameter of the holes, said rotation pin fitted in the holes.

9. The element according to claim 3, further comprising:
notches (50) made on said clip tab (12) forming position references for an elastic ring (52).

10. A vascular clip comprised of:
an assembly of two identical said elements of claim 9, the two elements being assembled in such a way that one of the two brackets (21, 22) of a first of the two elements is fitted between two brackets (21', 22') of a second of the two elements and that axes of holes (23, 24, 23', 24') of the four brackets are collinear; and
a rotation pin (60) with a diameter equal to a diameter of the holes, said rotation pin fitted in the holes.

11. A vascular clip comprised of:
an assembly of two identical said elements of claim 3, the two elements being assembled in such a way that one of the two brackets (21, 22) of a first of the two elements is fitted between two brackets (21', 22') of a second of the two elements and that axes of holes (23, 24, 23', 24') of the four brackets are collinear; and
a rotation pin (60) with a diameter equal to a diameter of the holes, said rotation pin fitted in the holes.

12. The element according to claim 2, further comprising:
notches (50) made on said clip tab (12) forming position references for an elastic ring (52).

13. A vascular clip comprised of:
an assembly of two identical said elements of claim 12, the two elements being assembled in such a way that one of the two brackets (21, 22) of a first of the two elements is fitted between two brackets (21', 22') of a second of the two elements and that axes of holes (23, 24, 23', 24') of the four brackets are collinear; and
a rotation pin (60) with a diameter equal to a diameter of the holes, said rotation pin fitted in the holes.

14. The vascular clip according to claim 13, further comprising:
at least one elastic ring (52) that externally surrounds the clip tabs of the two assembled elements, said elastic ring being located in one of the notches (50).

15. A vascular clip comprised made of:
an assembly of two identical said elements of claim 2, the two elements being assembled in such a way that one of the two brackets (21, 22) of a first of the two elements is fitted between two brackets (21', 22') of a second of the two elements and that axes of holes (23, 24, 23', 24') of the four brackets are collinear; and
a rotation pin (60) with a diameter equal to a diameter of the holes, said rotation pin fitted in the holes.

16. The element according to claim 1, further comprising:
notches (50) made on said clip tab (12) to make position references for an elastic ring (52).

17. A vascular clip comprised made p of:
an assembly of two identical said elements of claim 16, the two elements being assembled in such a way that one of the two brackets (21, 22) of a first of the two elements is fitted between two brackets (21', 22') of a second of the two elements and that axes of holes (23, 24, 23', 24') of the four brackets are collinear; and
a rotation pin (60) with a diameter equal to a diameter of the holes, said rotation pin fitted in the holes.

18. The vascular clip according to claim 17, further comprising:
at least one elastic ring (52) that externally surrounds the two clip tabs of the two assembled elements, said elastic ring being located in one of the notches (50).

19. The vascular clip according to claim 18, wherein said elastic ring (52) has a shape configured to apply radial tensile force in a given value T that is substantially based on the formula:

$$T = \frac{-2E(R - Ro)}{Ro}$$

wherein E is the Young's modulus of the elastic material, and Ro and R are average radii of the elastic ring when unstrained and strained, respectively.

20. A vascular clip comprised of:
an assembly of two identical said elements of claim 1, the two elements being assembled in such a way that one of the two brackets (21, 22) of a first of the two elements is fitted between two brackets (21', 22') of a second of the two elements and that axes of holes (23, 24, 23', 24') of the four brackets are collinear; and
a rotation pin (60) with a diameter equal to a diameter of the holes, said rotation pin fitted in the holes.

* * * * *